(12) United States Patent
Ikeda et al.

(10) Patent No.: US 6,225,078 B1
(45) Date of Patent: *May 1, 2001

(54) METHOD FOR QUANTITATIVE MEASUREMENT OF A SUBSTRATE

(75) Inventors: Shin Ikeda, Katano; Toshihiko Yoshioka; Shiro Nankai, both of Hirakata, all of (JP)

(73) Assignee: Matsushita Electric Industrial Co., Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/122,591

(22) Filed: Jul. 27, 1998

(30) Foreign Application Priority Data

Jul. 29, 1997 (JP) .................................................. 9-203371

(51) Int. Cl.⁷ ....................................................... C12Q 1/26
(52) U.S. Cl. ................................ 435/25; 435/14; 204/403
(58) Field of Search ................................ 435/14, 25, 28; 204/403, 412, 415

(56) References Cited

U.S. PATENT DOCUMENTS

| | | |
|---|---|---|
| 3,886,045 | 5/1975 | Meiattini . |
| 5,288,636 * | 2/1994 | Pollmann et al. ................... 435/288 |
| 5,378,332 | 1/1995 | Pandey . |
| 5,582,697 * | 12/1996 | Ikeda et al. ........................... 204/403 |
| 5,650,062 * | 7/1997 | Ikeda et al. ........................... 205/778 |
| 5,658,443 * | 8/1997 | Yamamoto et al. .................. 204/403 |
| 5,863,400 * | 1/1999 | Drummond et al. ................. 204/415 |

FOREIGN PATENT DOCUMENTS

| | | |
|---|---|---|
| 0 732 406 * | 9/1996 | (EP) . |
| 3-202764 * | 9/1991 | (JP) . |
| WO 84/03562 * | 9/1984 | (WO) . |
| WO95/00662 | 1/1995 | (WO) . |

OTHER PUBLICATIONS

Simultaneous Use of Dehydrogenases and Hexacyanoferrate(III) Ion in Electrochemical Biosensors for L–Lactate, D–Lactate and L–Glutamate Ions, Analytica Chimica Acta 278:25–33, 1993.*

* cited by examiner

*Primary Examiner*—Ralph Gitomer
(74) *Attorney, Agent, or Firm*—McDermott, Will & Emery

(57) ABSTRACT

The invention provides a method for quantitative measurement of a substrate with high accuracy by electrochemically oxidizing an electron mediator which has been reduced by enzyme reaction thereby determining the substrate concentration based on a current flowing during electrochemical oxidation from which adverse effects of an easy-to-oxidize substance on the oxidation process have been minimized. The quantitating method in accordance with the present invention comprises a first step for causing a substrate contained in a sample to react with a specific oxidoreductase to the substrate in the presence of an electron mediator in oxidized state, and a second step for electrochemically reducing the electron mediator in oxidized state which remains non-reduced by the enzyme reaction in the first step, thereby obtaining a current flowing during electrochemical reduction.

6 Claims, 6 Drawing Sheets

METHOD FOR QUANTITATIVE MEASUREMENT OF A SUBSTRATE

BACKGROUND OF THE INVENTION

The present invention relates to a method for rapid and easy quantitative measurement of a substrate contained in a sample such as blood, urine and fruit juice with high accuracy.

A conventional simple method for quantitating a specific component in a sample solution with no dilution or agitation of the sample solution is to cause the specific component to react with an oxidoreductase whose substrate corresponds to the specific component in the presence of an electron mediator or electron acceptor, followed by electrochemical oxidation of the electron mediator which has been reduced by this enzyme reaction, thereby to determine the oxidation current flowing during this electrochemical oxidation.

This method normally uses a biosensor as disclosed in the Japanese Laid-Open Patent Publication Hei 3-202764.

The biosensor is produced by first forming an electrode system having a working electrode and a counter electrode on an electrically insulating base plate by a screen printing method or the like, subsequently forming a reaction layer including an oxidoreductase and an electron mediator above the electrode system, and finally bonding a cover and a spacer to the electrically insulating base plate.

With this biosensor, various specific components can be quantitated by varying the oxidoreductase.

Here, a glucose sensor will be described as an example of biosensor.

Conventionally known method for quantitative measurement of glucose is a system comprising a combination of glucose oxidase with an oxygen electrode or a hydrogen peroxide electrode (e.g., "Biosensor", ed. by Shuichi Suzuki, Kodansha, Japan).

Glucose oxidase selectively oxidizes a substrate β-D-glucose to D-glucono-δ-lactone by utilizing oxygen dissolved in a sample solution as an electron mediator. When the substrate is oxidized by the glucose oxidase, the oxygen used as the electron mediator is reduced to hydrogen peroxide. The glucose concentration can be quantitated either by measurement of the volume of oxygen consumed during this reaction using an oxygen electrode or by measurement of the volume of hydrogen peroxide produced using a hydrogen peroxide electrode of platinum or the like.

However, this method has a drawback that the measurement is largely affected by the concentration of oxygen contained in a sample solution, depending on the measuring object. This system has another drawback that the system cannot function in the absence of oxygen.

To overcome these problems, a type of glucose sensor has been developed which includes an organic compound or a metal complex such as potassium ferricyanide, ferrocene derivatives, quinone derivatives, etc. as electron mediator, in place of oxygen.

This biosensor can carry a known amount of glucose oxidase on an electrode system, together with an electron mediator in their stabilized state. As a result, the electrode system can be integrated with the reaction layer almost in dry state.

Such biosensor is normally disposable and facilitates measurement of the concentration of glucose by a simple instillation of a measuring sample at a sensor chip mounted in a measurement device. Therefore, this biosensor has been attracting much attention recently.

As described above, the substrate in a sample can be quantitated based on the current flowing across the electrodes during oxidation of the electron mediator which has been reduced by a series of enzyme reaction.

If the oxidation current value is measured with a two-electrode system comprising a working electrode and a counter electrode, then the presence of an electron mediator in oxidized state which must be reduced on the counter electrode becomes mandatory.

When the measuring sample is predicted to have a low concentration of substrate, it becomes unnecessary to secure the presence of such electron mediator in oxidized state, because the amount of oxidized electron mediator to be reduced by enzyme reaction is small.

However, when the measuring sample is predicted to have a high concentration of substrate, most of the electron mediator in oxidized state is reduced by enzyme reaction, resulting in a deficiency of oxidized electron mediator which can be reduced on the counter electrode. This renders the reduction on the counter electrode to show a rate-determining step, affecting the resultant current value.

Moreover, depending on sample, an easy-to-oxidize substance may be present that is oxidized to induce an oxidation current at the same time when the electron mediator in reduced state is oxidized on the electrode, producing a positive error in the current value measured. Furthermore, a high concentration of substrate may vary the oxidation current value.

BRIEF SUMMARY OF THE INVENTION

The object of the present invention is therefore to provide a method for high accuracy quantitative measurement of a substrate in a wide range of substrate concentration, particularly in high substrate concentrations by suppressing the effect on the current value of a deficiency of electron mediator in oxidized state to be reduced on the counter electrode and minimizing adverse effects of an easy-to-oxidize substance on the current value.

The present invention provides a method for quantitative measurement of a substrate comprising:

a first step for causing a substrate contained in a sample to react with a specific oxidoreductase to the substrate in the presence of an electron mediator in oxidized state, and a second step for electrochemically reducing the electron mediator in oxidized state which remains non-reduced by the enzyme reaction in the first step, thereby obtaining a current flowing during the electrochemical reduction.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
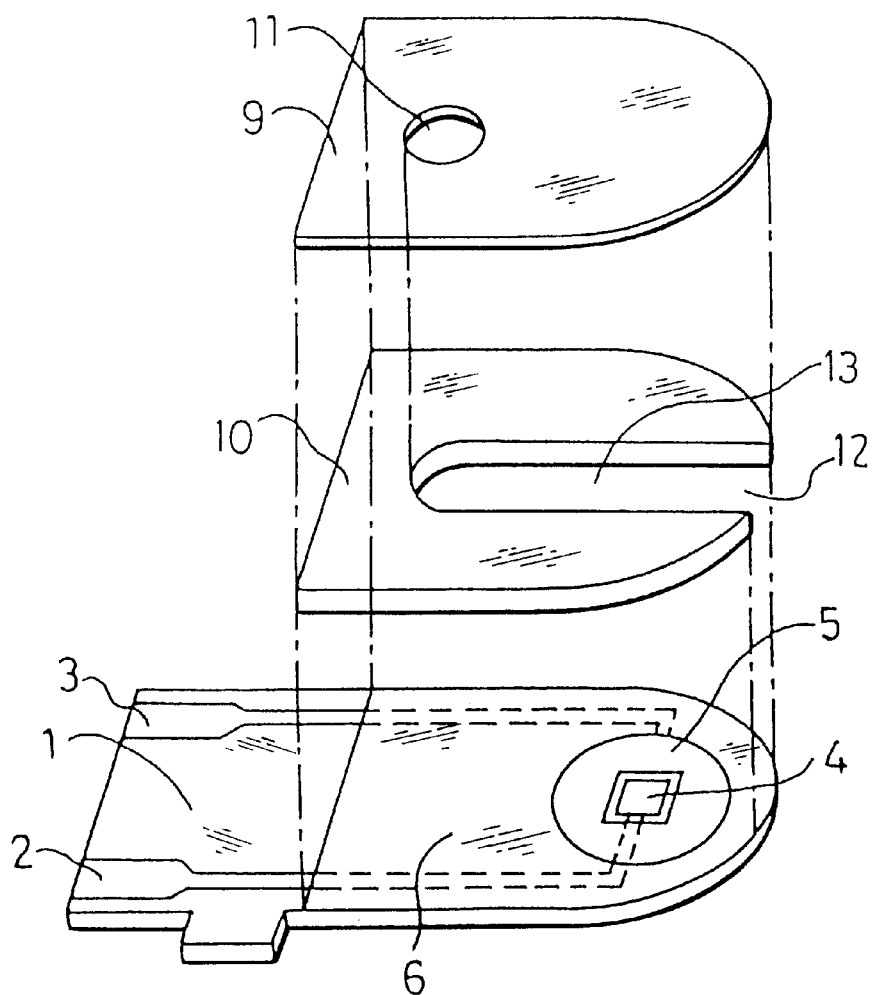
FIG. 1 is an exploded perspective view of a two-electrode system glucose sensor with an omission of the reaction layer in one example to which the present invention has been applied.

The easy-to-oxidize substances include ascorbic acid and uric acid contained in blood. Such substances resist electrochemical reduction and would not generate reduction current.

Therefore, by the method where the substrate concentration is quantitated by reducing electron mediator in oxidized state which remains non-reduced by a series of enzyme reaction and reading the resultant reduction current flowing during the reduction process, the adverse effect of the easy-to-oxidize substance can be minimized, thereby realizing higher accuracy quantitation of a substrate.

From the aspect of the oxidation-reduction occurring on the electrodes, if the two-electrode system is applied for measurement of the reduction current value, the oxidation of the electron mediator in reduced state shows the rate-determining step due to a small volume of electron mediator which has been reduced by the enzyme reaction if the substrate concentration is low. The reduction current value, therefore, increases with the increases in the substrate concentration.

Since the electron mediator in oxidized state decreases as the concentration of the substrate increases, the electron mediator in oxidized state becomes deficient at a certain concentration of substrate. Therefore, in the oxidation-reduction occurring on the electrodes, the reduction of the electron mediator in oxidized state shows the rate-determining step, manifesting decreased reduction current value.

The reduction current value during this process is an exact reflection of the amount of electron mediator in oxidized state which failed to be reduced by the enzyme reaction, thus demonstrating exceptional response characteristics to the concentration of substrate.

Even at low substrate concentrations, it is preferred that an electron mediator in reduced state is added to the enzyme reaction system where the substrate is reacted with an enzyme (oxidoreductase) in the presence of an electron mediator in oxidized state, in order to render the reduction of the electron mediator in oxidized state to show the rate-determining step. Participation of electron mediator in reduced state in the enzyme reaction system facilitates high accuracy quantitation of a substrate in a wider range of substrate concentrations.

The method for measurement of the reduction current value includes the two-electrode system having a working electrode and a counter electrode and a three-electrode system further having a reference electrode. The latter permits more accurate quantitative measurement of a substrate at higher concentrations.

Application of the method for quantitative measurement of a substrate in accordance with the present invention to a biosensor comprising an electrode system having at least a working electrode and a counter electrode formed on an electrically insulating base plate, and a reaction layer formed on the electrode system and including at least an oxidoreductase realizes high accuracy quantitation of a specific component contained in a body sample and thus preferable.

Further inclusion of a hydrophilic polymer in the reaction layer is preferable because it is helpful for preventing adsorption of protein or the like in the sample onto the surface of the electrode system.

Coating of the surface of the reaction layer with a layer containing lipid helps smooth supply of a sample to the reaction layer. This lipid coating may be applied if occasion demands.

A pH buffer may further be included in the reaction layer in order to increase the enzyme activity in the reaction layer.

Applicable oxidoreductase may be exemplified as glucose oxidase, glucose dehydrogenase, lactate oxidase, lactate dehydrogenase, uricase, fructose dehydrogenase, alcohol oxidase, cholesterol oxidase, xanthine oxidase, amino acid oxidase and the like.

A combination of plural oxidoreductases may also be used, such as glucose oxidase plus invertase, glucose oxidase plus invertase plus mutarotase, fructose dehydrogenase plus invertase, or the like.

As the electron mediator, potassium ferricyanide, p-benzoquinone, phenazine methosulfate, methylene blue, ferrocene derivatives, or the like may be used. The use of oxygen for electron mediator can yield a similar sensor response. Those electron mediators are used singly or in combination (a combination of two or more).

Applicable hydrophilic polymer may be exemplified as carboxymethyl cellulose, polyvinyl pyrrolidone, polyvinyl alcohol, gelatin and its derivative, a polymer of acrylic acid or an acrylate, a polymer of methacrylic acid or a methacrylate, starch and its derivative, a polymer of maleic anhydride or a maleate, cellulose derivatives such as hydroxypropyl cellulose, methyl cellulose, ethyl cellulose, hydroxyethyl cellulose, ethylhydroxyethyl cellulose, carboxymethylethyl cellulose or the like, polyamino acid such as polylysine, and polystyrene sulfonate.

Among them, carboxymethyl cellulose, hydroxyethyl cellulose, hydroxypropyl cellulose, methyl cellulose, ethyl cellulose, ethylhydroxyethyl cellulose and carboxymethylethyl cellulose are preferred. Polyamino acid such as polylysine, polyvinyl alcohol and polystyrene sulfonate may also be used preferably.

As the lipid, any amphipathic phospholipid such as lecithin, phosphatidylcholine, phosphatidylethanolamine or the like may be used preferably.

The pH buffer may be exemplified as potassium dihydrogen phosphate-dipotassium phosphate, potassium dihydrogen phosphate-disodium phosphate, sodium dihydrogen phosphate-dipotassium phosphate, sodium dihydrogen phosphate-disodium phosphate, citric acid-disodium phosphate, citric acid-dipotassium phosphate, citric acid-trisodium citrate, citric acid-tripotassium citrate, potassium dihydrogen citrate-sodium hydroxide, sodium dihydrogen citrate-sodium hydroxide, sodium hydrogen maleate-sodium hydroxide, potassium hydrogen phthalate-sodium hydroxide, succinic acid-sodium tetraborate, maleic acid-tris(hydroxymethyl)aminomethane, tris(hydroxymethyl)aminomethane-tris(hydroxymethyl)aminomethane hydrochloride, [N-(2-hydroxyethyl)piperazine-N'-2-ethanesulfonic acid]-sodium hydroxide, [N-tris(hydroxymethyl)methyl-2-aminoethanesulfonic acid]-sodium hydroxide, [piperazine-N,N'-bis(2-ethanesulfonic acid)]-sodium hydroxide and the like.

Those enzymes and electron mediators may be dissolved in a sample solution or otherwise isolated from the sample solution by fixing the enzyme layer containing those constituents to the base plate so as to avoid their direct dissolution in the sample solution. If the latter configuration is selected, it is preferable for the reaction layer to further include a hydrophilic polymer.

In the following, the present invention will be described more specifically referring to concrete embodiments.

FIG. 1 shows an exploded perspective view of a two-electrode system glucose sensor with an omission of the reaction layer. A silver paste is printed on an electrically insulating base plate 1 of polyethylene terephthalate by the screen printing method so as to form leads 2 and 3 on the base plate 1. Subsequently, a conductive carbon paste containing a resin binder is printed on the base plate 1 so as to form a working electrode 4. The working electrode 4 is in contact with the lead 2. Then, an electrically insulating layer 6 is further formed on the base plate 1 by printing thereon an insulating paste. The electrically insulating layer 6 covers the periphery of the working electrode 4 so as to hold the exposed area of the working electrode 4 constant. Thereafter, a conductive carbon paste containing a resin binder is printed on the base plate 1 so as to cause the carbon paste to contact the previously formed lead 3, which formed a ring-like counter electrode 5.

Then, the electrically insulating base plate 1, a cover 9 having an air vent 11 and a spacer 10 are bonded to each other in a positional relationship as shown by the dotted chain line in FIG. 1, which gives a biosensor used as a glucose sensor. The spacer 10 has a slit 13 for forming a sample supply path between the base plate and the cover. Numeral 12 corresponds to an opening of the sample supply path.

Figure 2:
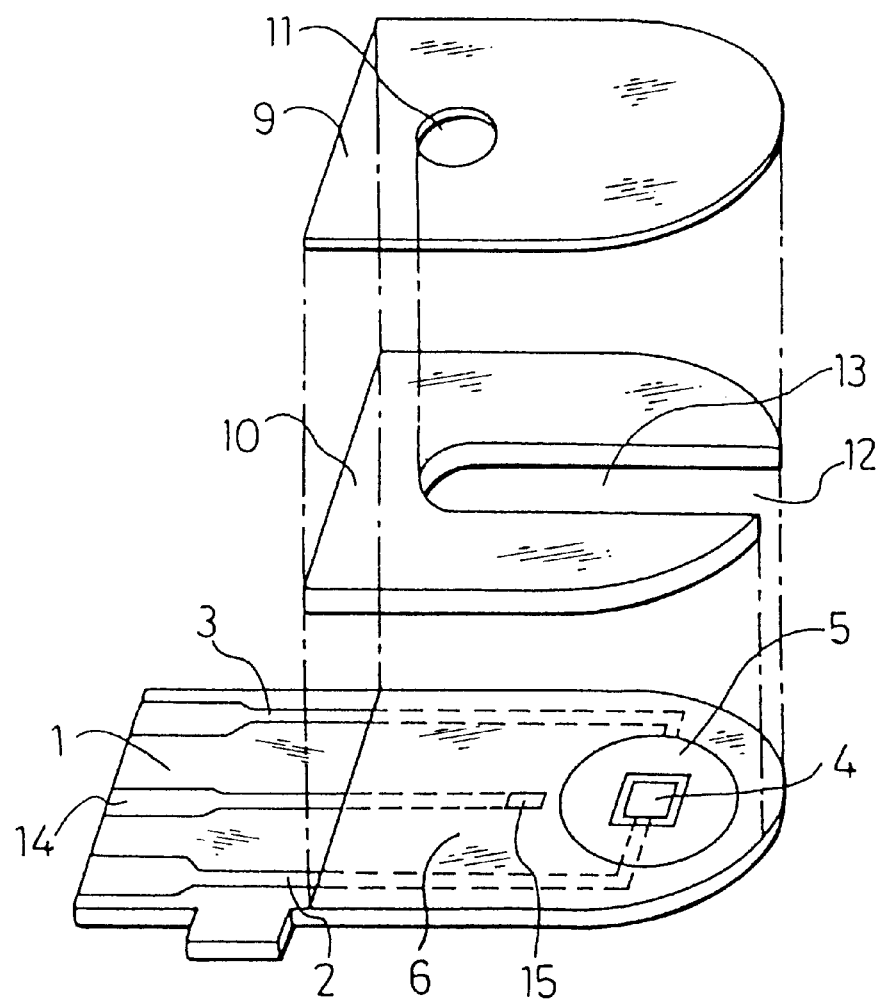
FIG. 2 is an exploded perspective view of a three-electrode system glucose sensor with an omission of the reaction layer in one example to which the present invention has been applied.

FIG. 2 shows an exploded perspective view of a three-electrode system glucose sensor with an omission of the reaction layer. This glucose sensor has the same configuration as that of FIG. 1, except that the glucose sensor further comprises a reference electrode 15 made of a carbon paste formed outside the periphery of the counter electrode 5 so as to be exposed from the electrically insulating layer 6, and a lead 14 for the reference electrode.

Figure 3:
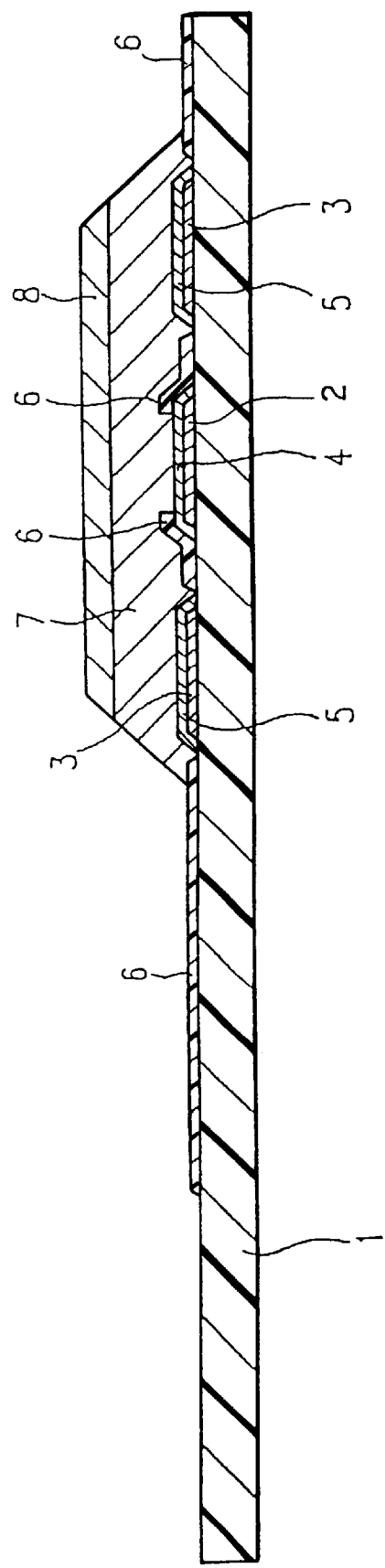
FIG. 3 is a longitudinal cross-sectional view of the vital part of the same glucose sensor from which the spacer and the cover have been omitted.

FIG. 3 is a longitudinal cross-sectional view showing the vital part of a biosensor used in one example for application of the present invention, with an omission of the spacer and the cover.

A reaction layer 7 including an enzyme and an electron mediator is formed on the electrically insulating base plate 1 above which the electrode system has been formed as shown in FIG. 1, and a lecithin layer 8 is further formed on the reaction layer 7.

EXAMPLE 1

In this example, the reaction layer was formed by dropping a mixed aqueous solution of glucose oxidase (EC1.1.3.4; hereinafter referred to as "GOD") with potassium ferricyanide on the electrode system formed on the base plate 1 in FIG. 1 and drying it. Then, the lecithin layer was formed by dropping a toluene solution of lecithin on the reaction layer and drying it.

The cover 9 and the spacer 10 were then bonded to the base plate 1 in a positional relationship shown by the dotted line in FIG. 1, which gave a glucose sensor used in this example.

Glucose standard solutions at various concentrations were then formulated as sample solutions. Each of those aqueous glucose standard solutions (3 μl) was supplied to the glucose sensor from the opening 12 of the sample supply path. The sample solution advanced to the air vent 11 and dissolved the reaction layer 7 and the lecithin layer above the electrode system. Upon dissolution of the reaction layer 7, enzyme reaction where glucose contained in the sample solution is oxidized to gluconolactone by the GOD will take place. This enzyme reaction accompanies at the same time reduction of the potassium ferricyanide to potassium ferrocyanide to produce ferrocyanide ions.

When a certain time had lapsed after supply of the sample solution, a voltage of −1.0 V was applied to the working electrode with reference to the counter electrode 5, which induced reduction of the potassium ferricyanide on the working electrode and oxidation of the potassium ferrocyanide on the counter electrode to generate a current flow across the electrodes. The current flowing during this oxidation-reduction was read 5 seconds after application of the voltage.

Figure 4:
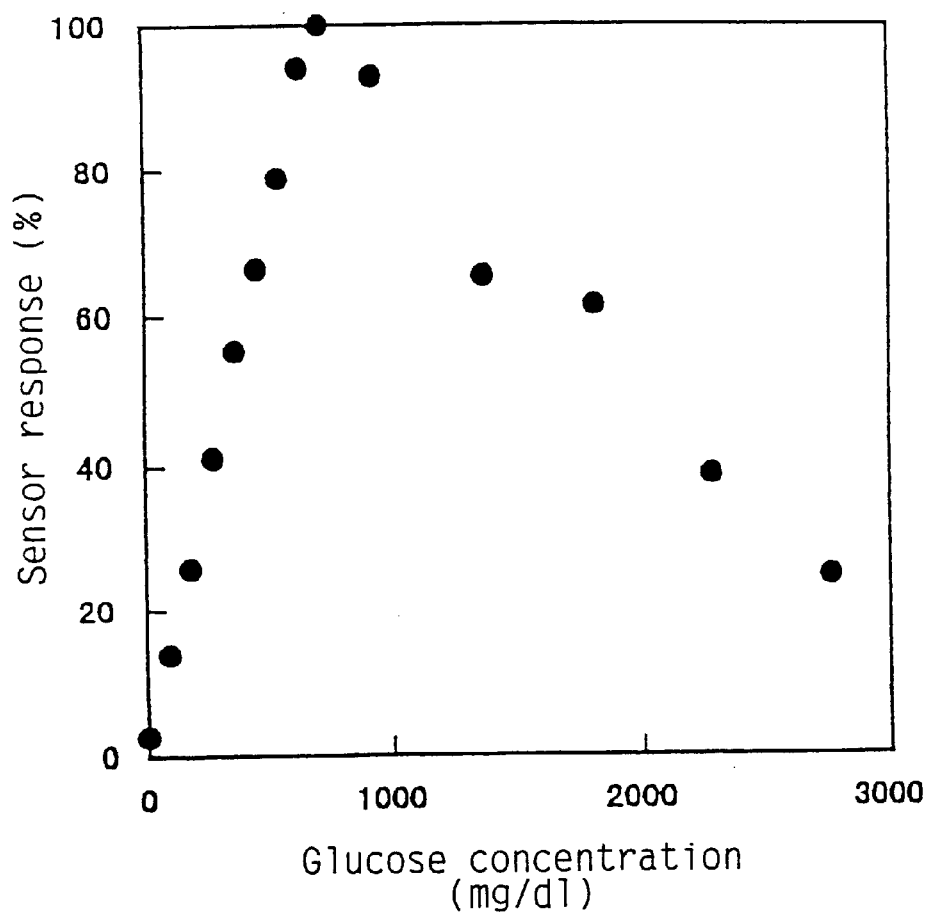
FIG. 4 illustrates the characteristics of the response of a two-electrode system glucose sensor to various glucose standard solutions in one example to which the present invention has been applied.

FIG. 4 shows the sensor responses to the various aqueous glucose standard solutions by defining the current value at a glucose concentration of about 700 mg/dl as 100%.

The sensor response showed linear increases with the increases in the glucose concentrations in a range of 0 to 700 mg/dl. This suggests the rate-determining step of the oxidation of the potassium ferrocyanide on the counter electrode due to small amounts of ferrocyanide ions produced by the enzyme reaction.

The sensor response decreased as the glucose concentrations increased above 700 mg/dl. This indicates the rate-determining step of the reduction of the ferricyanide ions on the working electrode because of sufficiently large amounts of the ferrocyanide ions produced by the enzyme reaction.

As is evident from FIG. 4, the sensor showed excellent response characteristics irrespective of the glucose (substrate) concentrations.

EXAMPLE 2

In this example, an aqueous solution of carboxymethyl cellulose (hereinafter referred to as "CMC") was dropped on the electrode system above the base plate 1 in FIG. 1 and dried to form a CMC layer. Then, the reaction layer and the lecithin layer were formed in the same manner as in Example 1. The presence of the CMC layer minimizes the adverse effect on the measurement by adsorption of protein onto the surface of the electrodes.

A glucose sensor was produced in the same manner as in Example 1 and evaluated for its responses to various aqueous glucose standard solutions as formulated in Example 1. The sensor showed similar response characteristics to those of Example 1, with less variations.

EXAMPLE 3

In this example, the CMC layer was formed similarly by dropping an aqueous CMC solution on the electrode system above the base plate 1 in FIG. 1 and drying it. Then, a mixed aqueous solution of GOD, potassium ferricyanide and potassium ferrocyanide was dropped on the CMC layer and dried to form the reaction layer. A glucose sensor was produced in the same manner as in Example 1 and evaluated for its responses to various aqueous glucose standard solutions as formulated in Example 1.

Figure 5:
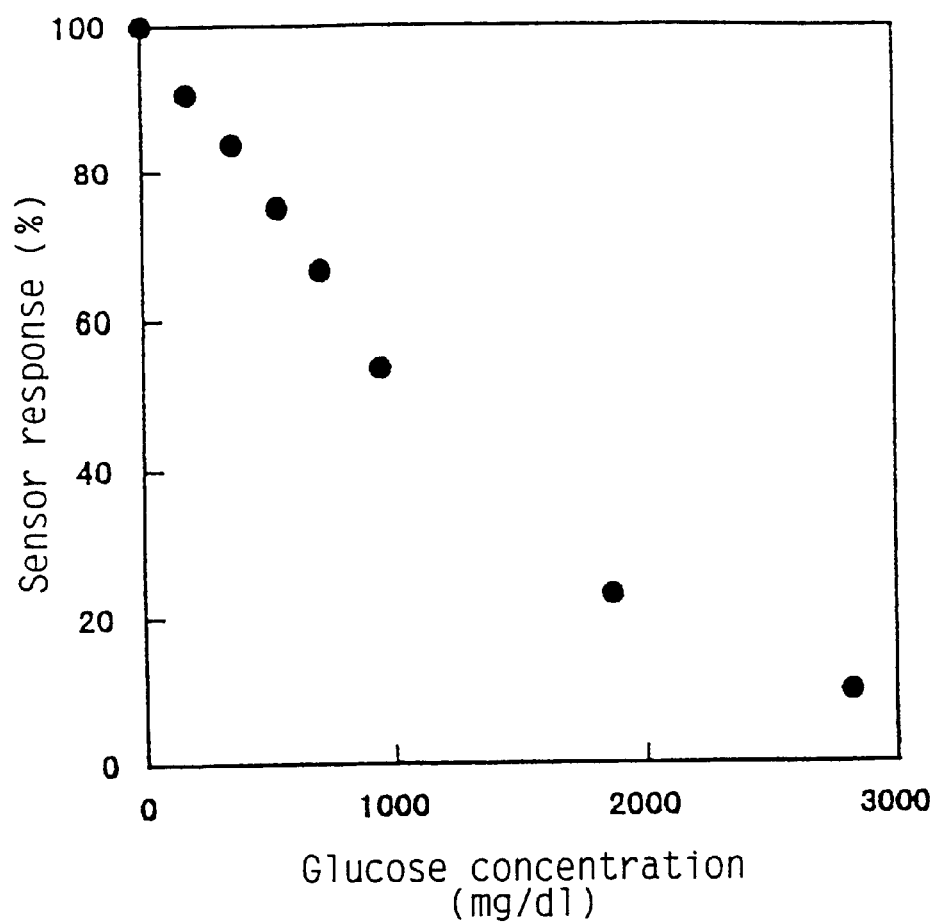
FIG. 5 illustrates the characteristics of the response of a two-electrode system glucose sensor to various glucose standard solutions in another example to which the present invention has been applied.

FIG. 5 summarizes the sensor responses to the various aqueous glucose standard solutions by defining the responsive current value to a solution including 0 mg/dl glucose as 100%.

As is seen from FIG. 5, the sensor response decreased as the glucose concentrations increased. The reason is that because potassium ferrocyanide coexisted in the reaction layer, the ferrocyanide ions to be oxidized on the counter electrode were always secured sufficiently, which ensured the rate-determining step of the reduction of ferricyanide ions on the working electrode even if the concentration of the substrate is low.

The sensor showed excellent response characteristics irrespective of the glucose (substrate) concentrations.

EXAMPLE 4

In this example, the CMC layer was formed by dropping an aqueous CMC solution on the electrode system above the electrically insulating base plate 1 in FIG. 2, while avoiding the reference electrode 15, and drying it. Then, a mixed aqueous solution of GOD and potassium ferricyanide was dropped on the CMC layer and dried to form the reaction layer, above which a toluene solution of lecithin was dropped and dried to form thereon the lecithin layer.

Then, the cover 9 and the spacer 10 were bonded to the base plate 1 in a positional relationship shown by the dotted chain line in FIG. 2, which gave a glucose sensor used in this example.

Each of the various aqueous glucose standard solutions (3 $\mu$l) formulated in Example 1 was supplied from the opening 12 of the sample supply path. When a certain time lapsed after supply of the sample solution, a voltage was applied onto the working electrode at a potential of –0.8 V using the reference electrode 15 as standard. And, 5 seconds after the voltage application, the current flowing across the working electrode 4 and the counter electrode 5 was measured.

Figure 6:
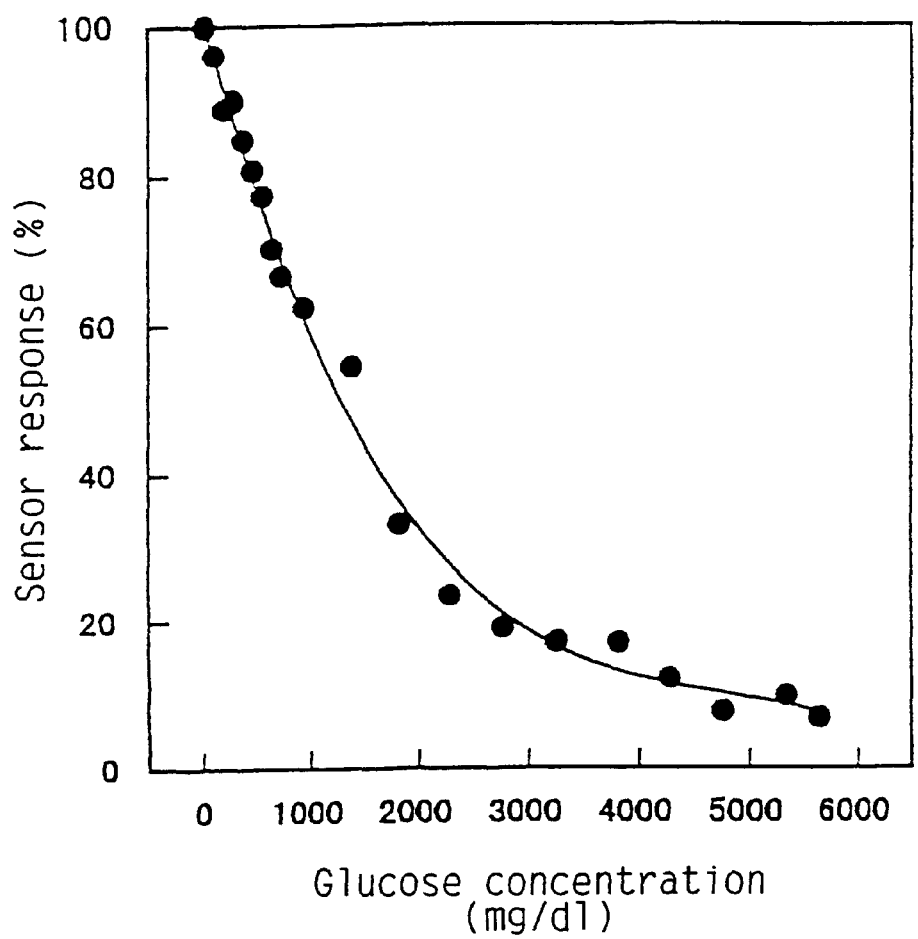
FIG. 6 illustrates the characteristics of the response of a three-electrode system glucose sensor to various glucose standard solutions in another example to which the present invention has been applied.

FIG. 6 summarizes the sensor responses to the various aqueous glucose standard solutions by defining the responsive current value to a solution including 0 mg/dl glucose as 100%.

As shown in FIG. 6, the sensor showed excellent response characteristics in a wide range of glucose (substrate) concentrations, permitting quantitation up to 6,000 mg/dl or so.

EXAMPLE 5

A glucose sensor was produced in the same manner as in Example 4.

Then, the sensor was evaluated for its responses in the same manner as in Example 4 except for the use of various aqueous glucose standard solutions formulated in Example 1 further containing known amounts of ascorbic acid as sample solutions.

The sensor showed substantially identical responses to those of the glucose sensor in Example 4 despite the presence of ascorbic acid, thus demonstrating excellent response characteristics.

In the foregoing examples, although conductive carbon paste and insulating paste were used to form printed patterns, the present invention is not limited to those.

As discussed above, according to the present invention, the concentration of a substrate can be quantitated with high accuracy in a wide range of substrate concentrations, particularly in high substrate concentrations.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for quantitative measurement of a substrate in a sample solution without interference from the presence of an easily oxidizable substance with a biosensor comprising an electrically insulating base plate, an electrode system having at least a working electrode and a counter electrode formed on said base plate, and a reaction layer including an oxidoreductase and an electron mediator in oxidized state disposed on said electrode system, said method comprising the steps of:

contacting the sample solution with said reaction layer to react the substrate with said oxidoreductase to produce reduced oxidoreductase, wherein said reduced oxidoreductase reacts with said electron mediator to cause a reduction of at least some of said electron mediator, wherein reduced and unreduced electron mediator are obtained, applying a voltage between the working electrode and the counter electrode to electrochemically reduce said unreduced electron mediator at the working electrode, and measuring a reduction current flowing between the working electrode and the counter electrode, thereby quantifying the substrate.

2. The method for quantitative measurement of a substrate in a sample solution in accordance with claim 1, wherein said electrode system further comprises a reference electrode.

3. The method for quantitative measurement of a substrate in a sample solution in accordance with claim 2, wherein said reaction layer further includes a hydrophilic polymer.

4. The method for quantitative measurement of a substrate in a sample solution in accordance with claim 2, wherein said reaction layer further includes additional electron mediator in reduced state to measure low concentrations of the substrate.

5. The method for quantitative measurement of a substrate in a sample solution in accordance with claim 1, wherein said reaction layer further includes a hydrophilic polymer.

6. The method for quantitative measurement of a substrate in a sample solution in accordance with claim 1, wherein said reaction layer further includes additional electron mediator in reduced state to measure low concentrations of the substrate.

* * * * *